(12) United States Patent
Devarasetty et al.

(10) Patent No.: US 11,464,460 B2
(45) Date of Patent: Oct. 11, 2022

(54) SYSTEMS, DEVICES, AND METHODS FOR DETECTING PHYSICAL DISTRESS IN INFANT TRACHEOSTOMY PATIENTS

(71) Applicants: Pratyush Pavan Devarasetty, Cary, NC (US); Sidney Hunter Rogers, Raleigh, NC (US); Conrad Carlyle Dear, Syria, VA (US); Ryan Terry Hobbs, Matthew, NC (US); Ethan Ryan Trull, Ellenboro, NC (US)

(72) Inventors: Pratyush Pavan Devarasetty, Cary, NC (US); Sidney Hunter Rogers, Raleigh, NC (US); Conrad Carlyle Dear, Syria, VA (US); Ryan Terry Hobbs, Matthew, NC (US); Ethan Ryan Trull, Ellenboro, NC (US)

(73) Assignees: Pratyush Pavan Devarasetty, Cary, NC (US); Sidney Hunter Rogers, Raleigh, NC (US); Conrad Carlyle Dear, Syria, VA (US); Ryan Terry Hobbs, Matthew, NC (US); Ethan Ryan Trull, Ellenboro, NC (US)

( * ) Notice: Subject to any disclaimer, the term of this patent is extended or adjusted under 35 U.S.C. 154(b) by 0 days.

(21) Appl. No.: 16/612,598

(22) PCT Filed: Oct. 21, 2019

(86) PCT No.: PCT/US2019/057160
§ 371 (c)(1),
(2) Date: Nov. 11, 2019

(87) PCT Pub. No.: WO2021/080551
PCT Pub. Date: Apr. 29, 2021

(65) Prior Publication Data
US 2022/0249032 A1    Aug. 11, 2022

(51) Int. Cl.
*A61B 5/00* (2006.01)
*G08B 21/04* (2006.01)
*G08B 21/18* (2006.01)

(52) U.S. Cl.
CPC ............ *A61B 5/746* (2013.01); *A61B 5/6804* (2013.01); *A61B 5/6822* (2013.01); *A61B 5/742* (2013.01);
(Continued)

(58) Field of Classification Search
CPC ....... A61B 5/76; A61B 5/6804; A61B 5/6822; A61B 5/742; A61B 2562/063; G08B 21/043; G08B 21/0453; G08B 21/182
See application file for complete search history.

(56) References Cited

U.S. PATENT DOCUMENTS 6,409,659 B1 * 6/2002 Warner .................... A61B 5/02
                                                      382/128
6,967,652 B1 * 11/2005 Nubling ................. A61B 5/339
                                                      345/440.1
(Continued)

FOREIGN PATENT DOCUMENTS

WO    WO 2017/086073 A1    5/2017

OTHER PUBLICATIONS

International Search Report Corresponding to International application No. PCT/US 2019/057160 dated Jan. 23, 2020.
(Continued)

*Primary Examiner* — Ojiako K Nwugo
(74) *Attorney, Agent, or Firm* — Jenkins, Wilson, Taylor & Hunt, P.A.

(57) ABSTRACT

Systems and methods for monitoring physiological indicators that a patient is in distress can include a distress monitor comprising a band configured to be placed about and in contact with a portion of a body of the patient; a plurality of
(Continued)

sensors configured to measure changes in the physiological indicators of the patient; and a controller contained within an electronics region of the band, the controller being electronically connected to each of the plurality of sensors to receive a respective output signal from each; and a display configured to receive an output signal from the controller and to display an alert when the patient is displaying indicators of physiological distress.

18 Claims, 8 Drawing Sheets

(52) U.S. Cl.
CPC ....... *G08B 21/043* (2013.01); *G08B 21/0453* (2013.01); *G08B 21/182* (2013.01); *A61B 2562/063* (2013.01)

(56) References Cited

U.S. PATENT DOCUMENTS

| | | | | |
|---|---|---|---|---|
| 2008/0146892 | A1* | 6/2008 | LeBoeuf | A61B 5/02 600/300 |
| 2010/0217099 | A1* | 8/2010 | LeBoeuf | A61B 5/021 600/301 |
| 2013/0080843 | A1 | 3/2013 | Stergiou et al. | |
| 2013/0174844 | A1 | 7/2013 | Doll et al. | |
| 2015/0173674 | A1 | 6/2015 | Hayes et al. | |
| 2016/0002221 | A1 | 1/2016 | Nuovo et al. | |
| 2016/0038038 | A1* | 2/2016 | Kovacs | A61B 5/318 600/301 |
| 2016/0054876 | A1* | 2/2016 | Robison | H04L 43/0876 715/772 |
| 2016/0270717 | A1* | 9/2016 | Luna | A61B 5/743 |
| 2017/0095011 | A1 | 4/2017 | Cobbett et al. | |
| 2017/0119989 | A1 | 5/2017 | White et al. | |
| 2017/0245769 | A1* | 8/2017 | Niehaus | A61B 5/117 |
| 2017/0319122 | A1* | 11/2017 | Wild | A61B 5/746 |
| 2018/0116607 | A1* | 5/2018 | Yu | A61B 5/02405 |
| 2018/0303396 | A1* | 10/2018 | Wild | G16H 50/70 |
| 2019/0015014 | A1 | 1/2019 | Lange | |
| 2019/0099114 | A1 | 4/2019 | Mouradian et al. | |
| 2019/0209022 | A1 | 7/2019 | Sobol et al. | |
| 2021/0007667 | A1* | 1/2021 | Thaveeprungsriporn | A61B 5/4884 |

OTHER PUBLICATIONS

Written Opinion of the International Searching Authority Corresponding to International application No. PCT/US2019/057160 dated Jan. 23, 2020.

* cited by examiner

SYSTEMS, DEVICES, AND METHODS FOR DETECTING PHYSICAL DISTRESS IN INFANT TRACHEOSTOMY PATIENTS

TECHNICAL FIELD

The subject matter herein generally relates to the field of biomedical systems, devices, and methods for aiding in managing the care of infant tracheostomy patients, more specifically, by detecting distress in such patients who are not able to provide any audible cue to caregivers regarding their distress.

BACKGROUND

Some patients require medical treatment involving a tracheostomy procedure, which is a medical procedure in which a tube is inserted, through an incision made in the patient's neck, directly into the trachea of the patient to allow for supportive respiration of the patients, whether active or passive. Such a tracheostomy procedure can be necessary, for example, when the normal breathing path is obstructed or otherwise impaired. While the tracheostomy tube is in place, it is generally not possible for patients to make any audible noise using the patient's vocal cords. In adults and older children, this tends to not be a significant problem in terms of ensuring that the patient receives other supportive care that is needed. However, in pediatric patients (e.g., young children, infants, newborns, etc.), the only reliable mechanism by which they are able to communicate distress, whether due to having a soiled diaper, being hungry or thirsty, and/or being tired, for example, is through crying to alert a caregiver that the pediatric patient is in distress. When a tracheostomy tube is installed, the audible sound that typically accompanies the pediatric patient's cries is not generated, leaving such vulnerable patients at increased risk of complications due to the general inability to adequately communicate to their caregiver(s) that they are in distress for some reason due to their inability to audibly cry.

It is believed that approximately 4,800 tracheostomies are performed annually on pediatric patients. Pediatric patients that have had a tracheostomy performed must be continuously monitored and attended to. However, the inability of such patients to utilize the most common physiological indicator of distress, crying, leaves these patients vulnerable to a lack of supportive care. Additionally, existing solutions are both very demanding in terms of requiring excessive amounts of hospital staffing resources and/or have significant incidence of false readings, leading to caregivers being fatigued due to excessive false alerts of patient distress. As such, a need exists that would allow for caregivers to be notified when a patient with a tracheostomy tube installed is experiencing distress, so that the proper supportive care can be administered prior to the onset of complications from the lack of provision of any needed supportive care.

SUMMARY

According to a first example aspect, a system for monitoring physiological indicators that a patient is in distress is provided, the system comprising a distress monitor comprising a band configured to be placed about and in contact with a portion of a body of the patient; a plurality of sensors configured to measure changes in the physiological indicators of the patient; and a controller contained within an electronics region of the band, the controller being electronically connected to each of the plurality of sensors to receive a respective output signal from each; and a display configured to receive an output signal from the controller and to display an alert when the patient is displaying indicators of physiological distress.

In some embodiments of the system, the patient is a pediatric patient with a tracheostomy tube installed in a trachea of the patient, so that the patient cannot verbally communicate distress.

In some embodiments of the system, the band comprises a passage formed through a thickness thereof, through which the tracheostomy tube can pass.

In some embodiments of the system, the plurality of sensors comprise a pulse sensor, an electromyography (EMG) sensor, a galvanic skin response (GSR) sensor, or any combinations of the pulse sensor, the EMG sensor, and the GSR sensor.

In some embodiments of the system, the EMG sensor comprises at least two electrodes arranged on opposite sides of the neck of the patient, the EMG sensor being configured to detect movement of muscles in the neck of the patient.

In some embodiments of the system, the pulse sensor is an optical heart rate sensor.

In some embodiments of the system, the GSR sensor comprises at least two electrodes in direct contact with a surface of a skin of the patient to detect changes in conductance in the skin in response to distress.

In some embodiments, the system comprises a wearable garment configured to secure a tracheostomy tube and the distress monitor to a neck of the patient.

In some embodiments of the system, the wearable garment is a tracheostomy tie configured to secure a tracheostomy tube and the distress monitor to a neck of the patient.

In some embodiments of the system, the wearable garment has a plurality of holes formed in a surface of which is arranged directly against the skin of the patient, so that electrodes of the EMG sensor, electrodes of the GSR sensor, and/or the pulse sensor are in direct contact with the skin of the patient.

In some embodiments of the system, the controller is configured to execute one or more algorithms to analyze an output signal of each of the plurality of sensors.

In some embodiments of the system, the display comprises a data processor configured to execute one or more algorithms to analyze an output signal of each of the plurality of sensors.

In some embodiments of the system, the algorithms comprise one or more of pattern recognition and thresholding.

In some embodiments of the system, the display is configured to display information regarding the physiological indicators of the patient and/or an alert when at least two physiological indicators indicate that the patient is in distress.

In some embodiments of the system, the alert is an audible alert, a visual alert, a haptic alert, or any combination thereof.

In some embodiments of the system, the distress monitor comprises a power source configured to supply power to the controller and/or the plurality of sensors.

In some embodiments of the system, the power source is one or more of a rechargeable battery, a supercapacitor, a disposable battery, an alternating current (AC) power source, and/or a direct current (DC) power source.

In some embodiments of the system, the controller is configured to generate an alert when the plurality of sensors are active but one or more of the plurality of sensors are not transmitting an output signal to the controller due to an improper installation of the distress monitor on the patient and/or one or more of the plurality of sensors is malfunctioning.

According to a second example aspect, a method of monitoring physiological indicators to detect when a patient is in distress is provided, the method comprising attaching a distress monitor to the patient, the distress monitor comprising a plurality of sensors contained within and/or on a surface of a band of the distress monitor; and a controller contained within an electronics region of the band, the controller being electronically connected to each of the plurality of sensors; the method comprising measuring, using the plurality of sensors, changes in the physiological indicators of the patient; and transmitting an output signal for each of the plurality of sensors to the controller; applying one or more algorithms to analyze the output signal for each of the plurality of sensors; and generating an alert when at least a plurality of the physiological indicators indicate that the patient is in distress.

In some embodiments of the method, the alert is transmitted to a display, the alert comprising one or more of an audible alert, a visual alert, a haptic alert, or any combination thereof.

In some embodiments of the method, the patient is a pediatric patient with a tracheostomy tube installed in a trachea of the patient, so that the patient cannot verbally communicate distress.

In some embodiments, the method comprises inserting the tracheostomy tube through a passage formed through a thickness of the band.

In some embodiments of the method, the plurality of sensors comprise a pulse sensor, an electromyography (EMG) sensor, a galvanic skin response (GSR) sensor, or any combinations of the pulse sensor, the EMG sensor, and the GSR sensor.

In some embodiments of the method, the EMG sensor comprises at least two electrodes arranged on opposite sides of the neck of the patient, the EMG sensor being configured to detect movement of muscles in the neck of the patient.

In some embodiments of the method, the pulse sensor is an optical heart rate sensor.

In some embodiments of the method, the GSR sensor comprises at least two electrodes in direct contact with a surface of a skin of the patient to detect changes in conductance in the skin in response to distress.

In some embodiments, the method comprises securing the distress monitor to a neck of the patient via a wearable garment.

In some embodiments of the method, the wearable garment is a tracheostomy tie that secures a tracheostomy tube and the distress monitor to a neck of the patient.

In some embodiments of the method, the wearable garment has a plurality of holes formed in a surface thereof which is arranged directly against the skin of the patient, the method comprising inserting the distress monitor within the wearable garment; and securing the wearable garment to the patient so that electrodes of the EMG sensor, electrodes of the GSR sensor, and/or the pulse sensor are in direct contact with the skin of the patient.

In some embodiments, the method comprises executing one or more algorithms to analyze an output of each of the plurality of sensors.

In some embodiments of the method, the display comprises a data processor, the method comprising transmitting an output of each of the plurality of sensors to the display; and executing, via the data processor, one or more algorithms to analyze each output signal of each of the plurality of sensors.

In some embodiments of the method, the algorithms comprise one or more of pattern recognition and thresholding.

In some embodiments, the method comprises displaying information on the display regarding the physiological indicators of the patient and/or an alert when at least two physiological indicators indicate that the patient is in distress.

In some embodiments of the method, the distress monitor comprises a power source that supplies power to the controller and/or the plurality of sensors.

In some embodiments of the method, the power source is one or more of a rechargeable battery, a supercapacitor, a disposable battery, an alternating current (AC) power source, and/or a direct current (DC) power source.

In some embodiments, the method comprises generating, using the controller, an alert when the plurality of sensors are active but one or more of the plurality of sensors are not transmitting an output signal to the controller due to an improper installation of the distress monitor on the patient and/or one or more of the plurality of sensors is malfunctioning.

BRIEF DESCRIPTION OF THE DRAWING

A full and enabling disclosure of the present subject matter is set forth more in the remainder of the specification, including, for example, by referencing the accompanying example figures, in which.

DETAILED DESCRIPTION

This specification discloses devices, systems, and methods for detecting physiological distress in a patient, particularly in a patient unable to communicate said distress with caregiver(s), which could include a pediatric patient (e.g., an infant or young child) with a tracheostomy tube installed, so that the caregiver(s) can provide any supportive, or palliative, care necessary for the wellbeing of the pediatric patient. Examples of such supportive care can include, without limitation, changing soiled personal care items (e.g., diapers), providing with food and/or liquid, comforting, and the like.

Among the benefits achieved through the implementation of such devices, systems, and methods is an increase in survival rates of patients (e.g., pediatric patients) with tracheostomies, an increase in the quality of in-home care provided to such patients, a decrease in "alarm fatigue" by caregivers due to a corresponding decrease in false readings, and a reduction in readmission of the patient due to complications from inadequate supportive care after being discharged from the hospital, but while still having the tracheostomy installed. For example, caregivers (e.g., parents) are able to provide high quality in-home care for their child, with the ability to know precisely when the child needs attention and without excessively checking on the child for fear of missing a period of distress. Alarm fatigue and false alarms can be reduced because, rather than relying on multiple alarms from any of a panoply of medical devices (e.g., CPAP, pulse rate monitor, and the like) having artificially-increased sensitivity settings in an attempt to detect patient distress that these systems were not intended to detect, the devices, systems, and methods disclosed herein generate an audible and/or visual alert to notify caregivers based on distress of the patient using an alarm generated by the detection of distress using multiple types of distress detection. The survival rates of pediatric patients with tracheostomies should also increase because caregivers suffering less fatigue and having lessened uncertainty about whether the patient is actually in distress will lead to supportive care being rendered when actually needed by the patient.

The devices, systems, and methods disclosed herein are capable of taking biometric readings, including heart rate, electromyography, and galvanic skin response, of patients to generate a notification that the patient is crying. The devices, systems, and methods disclosed herein are compatible with tracheotomy tubes, meaning that the devices, systems, and methods can be implemented in conjunction with such tracheotomy tubes, without needing to remove or significantly disturb any pre-installed tracheotomy tubes. While the devices, systems, and methods disclosed herein are discussed relative to pediatric patients having a tracheotomy tube installed, persons having ordinary skill in the art will understand that such devices, systems, and methods can be readily adapted for both older patients and also to detect physiological distress in patients having a condition that renders verbal communication (e.g., by speaking, crying, etc.) difficult or impossible, including, for example and without limitation, cerebral palsy, vocal cord paralysis, autism, stroke, muscular dystrophy, and trauma during birth.

Figure 1A:
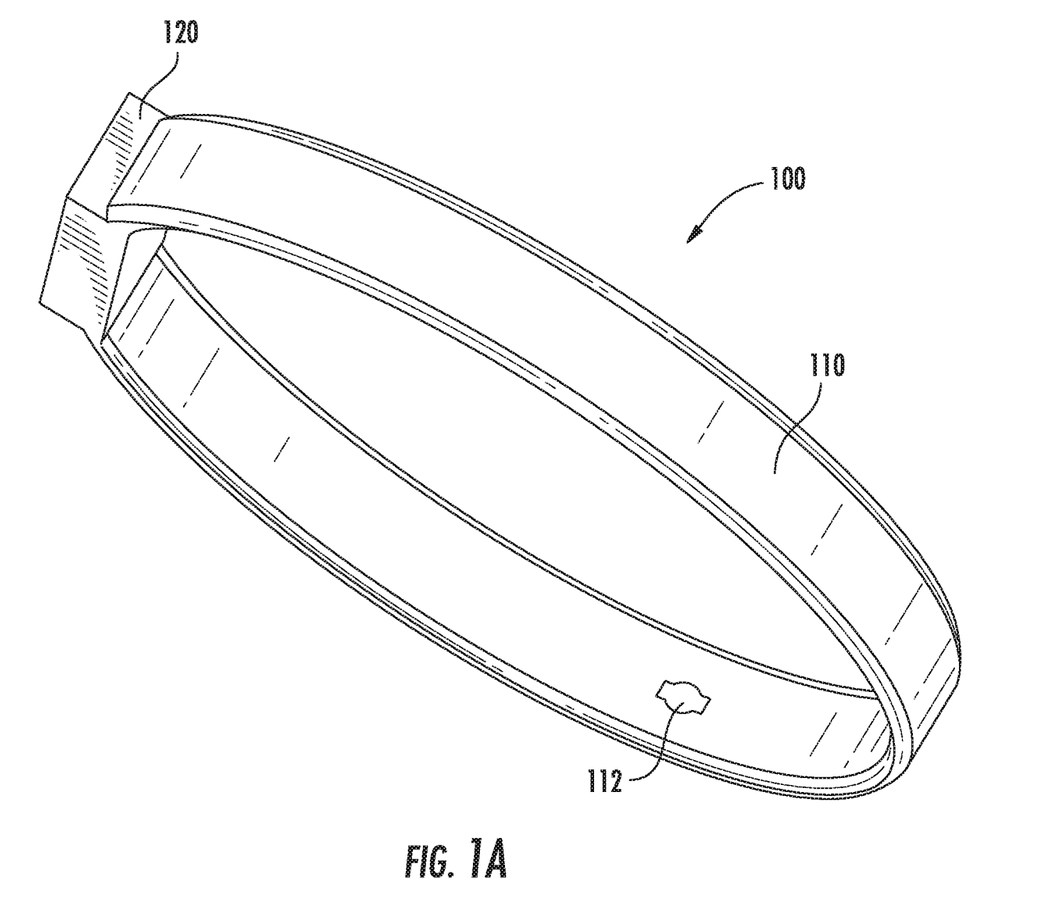
FIG. 1A is an isometric view of an example embodiment of a band that is wearable around a tracheostomy patient's neck to notify caregivers that the patient is in distress, in accordance with the disclosure herein.
Figure 1B:
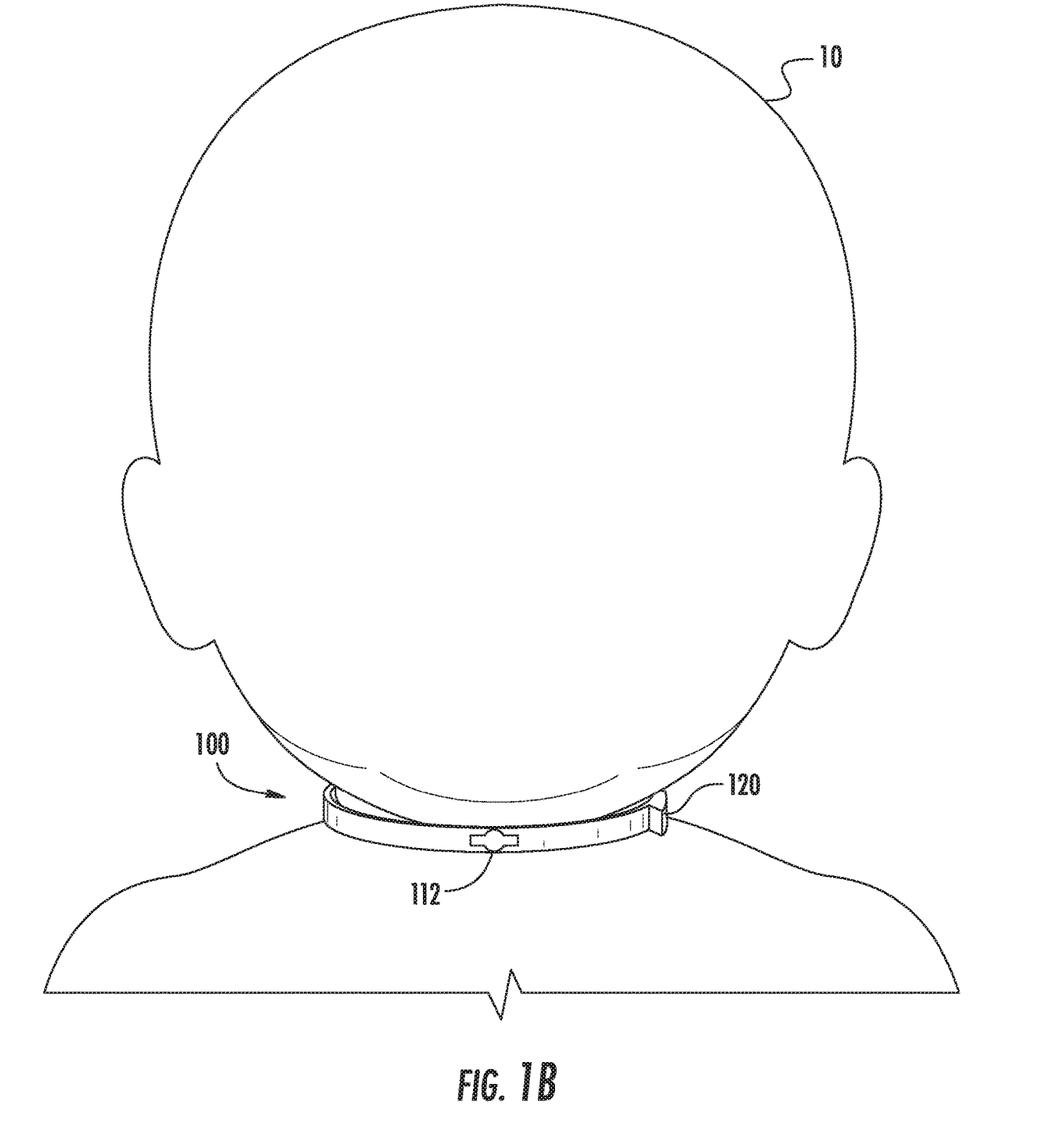
FIGS. 1B and 1C are respective top and side views of the band of FIG. 1A installed around the neck of a patient, here, an infant, in accordance with the disclosure herein.
Figure 1C:
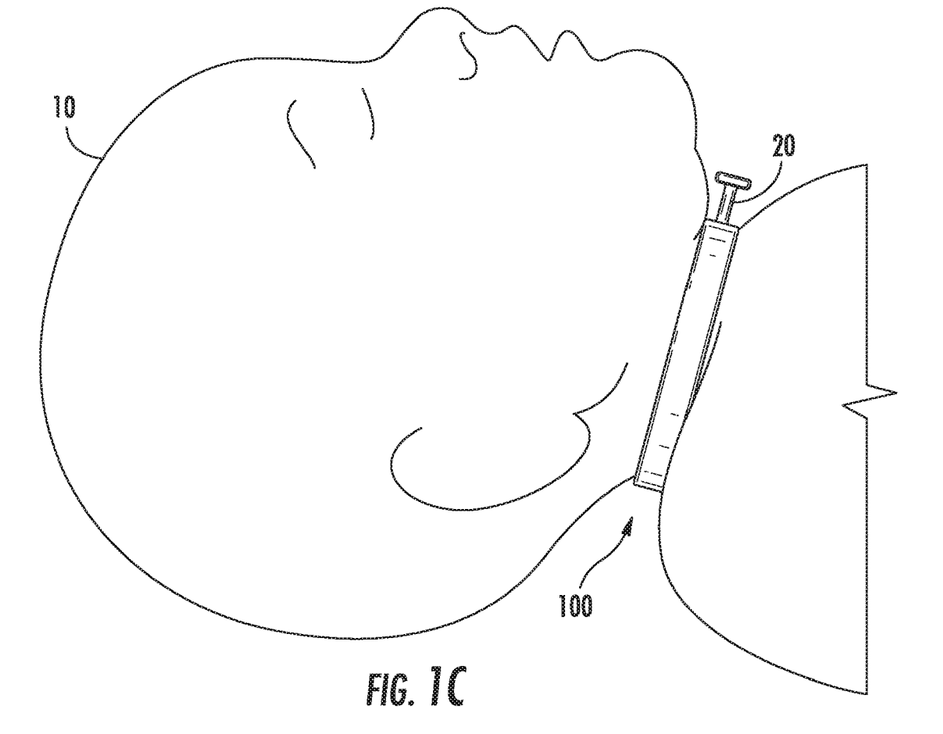
Figure 2:
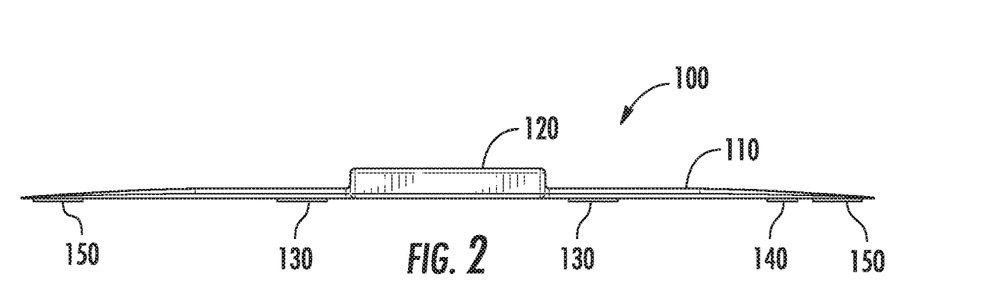
FIG. 2 is a side view of the band shown in FIG. 1A, in accordance with the disclosure herein.
Figure 3:
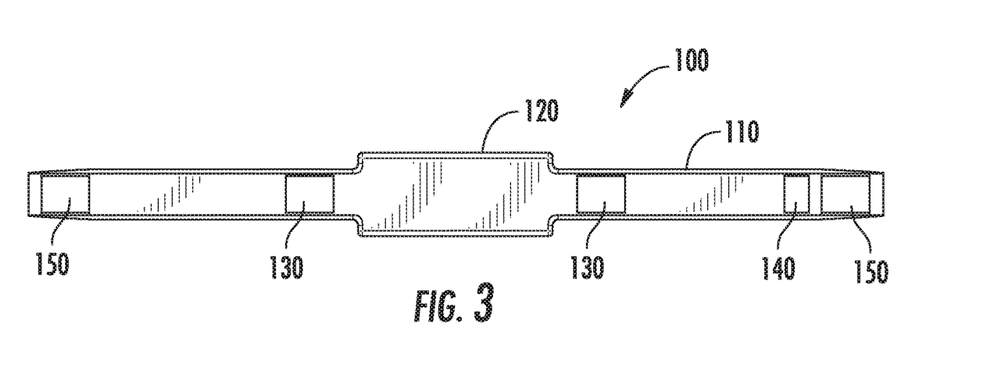
FIG. 3 is a rear view of the band shown in FIG. 1A, in accordance with the disclosure herein.
Figure 4:
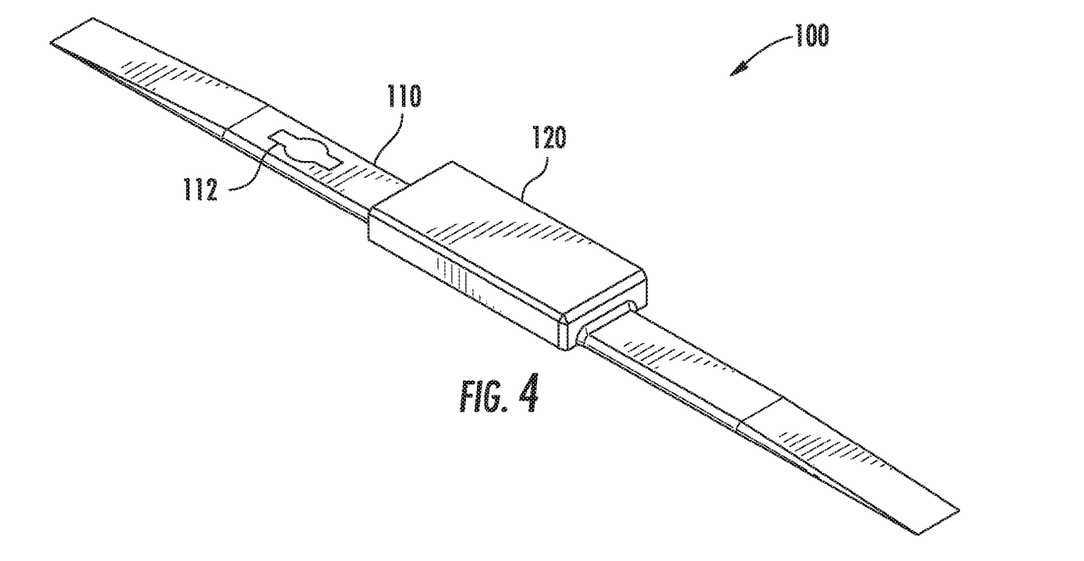
FIG. 4 is an isometric view of the band shown in FIG. 1A, in accordance with the disclosure herein.
Figure 5:
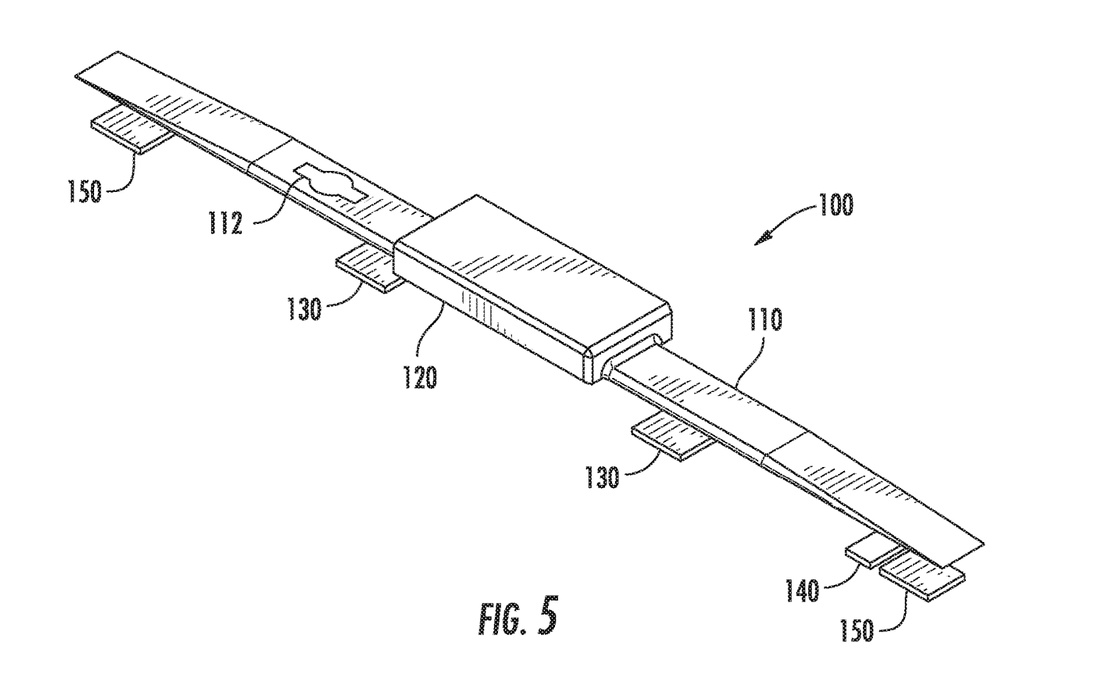
FIG. 5 is an exploded isometric view of the band shown in FIG. 1A, in accordance with the disclosure herein.

FIGS. 1A-1C show a distress monitor, generally designated 100, in an installed configuration (e.g., in ring, in which both ends of the band 110 are connected together about a portion of the body of the patient). The distress monitor 100 is shown in isolation in FIG. 1A and is shown installed around the neck of a pediatric tracheostomy patient 10 in FIGS. 1B and 1C. The distress monitor 100 has a band that fits securely about a portion, such as the neck, of a patient 10. The band 110 has a passage 112 formed through the entire thickness of the band 110 to allow for a tracheostomy tube 20 to pass therethrough without the tracheostomy tube 20 having to be removed to allow for installation of the distress monitor 100 around the neck of the patient 10.

The band 110 has fasteners at each end that are able to secure the band 110 around the neck of the patient 10 at any suitable length, thereby allowing the distress monitor 100 to be placed around any of a plurality of differently sized necks. By way of example, the fasteners can be hook-and-loop fabric attached to the band at attachment regions, one or more pins and a plurality of holes formed through the entire thickness of the band 110 to allow for the pin(s) to pass through any of the plurality of holes to allow for the band 110 to have substantially any desired length corresponding to a circumference of the neck of a patient 10 on which the distress monitor 100 is to be installed.

The band 110 can be made from any suitable material that will not cause pain, discomfort, or irritation to the skin of the patient 10, as the band 110 will be in place against the skin for a prolonged period of time during use. Examples of suitable materials include, for example, silicone and/or rubber. The passage 112 may have alignment and/or retention features that engage with corresponding features of the tracheostomy tube to ensure proper alignment and positioning of the tracheostomy tube during use of the distress monitor 100. The band has an electronics region 120, in which a controller (see 180, FIG. 10), power source (see 190, FIG. 10), and a communication device (see 186, FIG. 10) can be arranged. The communication device can use any suitable wireless communication protocol (e.g., Wi-Fi, Bluetooth, NFC, RFID, and the like) to transmit an alert regarding the patient's current level of distress to a display (200, FIG. 6). In order for the distress monitor 100 to be reusable, the power source may be a rechargeable battery and the distress monitor 100 may have a recharging port connected to the battery to allow for electricity to be provided thereto for recharging purposes.

While the example embodiment of the distress monitor 100 shown in FIGS. 1A-5 is configured to be attached to the neck of the patient 10, other embodiments of the distress monitor 10 may be arranged about another portion of the body of the patient 10 without deviating from the scope of the subject matter disclosed herein, including, for example, about the forehead of the patient 10.

The controller can be configured, for example, to control the state of charge of the power source, to indicate when the power source may be nearing depletion so that the distress monitor 100 can be replaced with a fully charged one, to receive signals from one or more sensors, or plurality of sensors, attached to the band 110 for monitoring for physiological indicators of distress, to compare the signals received from the sensor(s) against threshold values and/or apply algorithms to determine when one or more sensor(s) indicate the patient is in distress, to transmit one or more signals to the communication device, and/or to analyze the outputs of the sensor(s) to detect a malfunction of the distress monitor 100 so it can be replaced. In some embodiments, a button can be provided on the distress monitor 100 to allow for ease of linking or pairing the distress monitor 100 with the display (200, FIG. 6). In some embodiments, the controller can be a microcontroller that is integral to (e.g., molded within) the electronics region 120 of the band 110. In some embodiments, the microcontroller is an Arduino® microcontroller. In the embodiment shown in FIG. 10, the controller 180 comprises a processor 182, a memory 184, and, optionally, a wireless communication chip 186. In some embodiments, the controller 180 may also include a storage device (e.g., NAND storage, NVRAM, and the like).

FIGS. 2-5 show respective side, bottom, isometric, and exploded views of the distress monitor 100. In order to detect the physiological manifestations of the distress of the patient, the distress monitor 100 includes a plurality of sensors 130, 140, and 150. Sensors 130 are galvanic skin response sensors. Sensor 140 is a heart rate, or pulse, sensor. Sensors 150 are electromyography sensors. The sensors 130, 140, and 150 are electrically connected (e.g., directly or indirectly) to the controller and/or the power source. In some embodiments, the electrical connection between the sensors 130, 140, and 150 and the controller and/or the power source is made of flexible wires that can be, for example, formed on a surface of the band 110, embedded within the band 110, imprinted on a surface of the band 110, or by any suitable type of formation of such electrical connectors. In some embodiments, the electrical connectors are electrically conductive wires embedded entirely within the band 110 and/or the electronics region 120, so that the conductive wires between the sensors 130, 140, and 150 and the controller and/or power source are not visible outside of the distress monitor 100.

In some embodiments, the band 110 of the distress monitor 100 is inserted in the seams of a tie for a tracheostomy tube, the tie having cut-out regions that are arranged to face against the skin of the patient 10 when installed on the patient 10. The cut-out regions correspond to the positions of the electrodes of the EMG sensor 150, the electrodes of the GSR sensor 130, and/or the pulse sensor 140 along the band 110, such that the electrodes of the EMG sensor 150, the electrodes of the GSR sensor 130, and/or the pulse sensor 140 protrude through the cut-out regions of the tie to directly contact the skin of the patient 10 to obtain a signal for processing by the controller. In embodiments where the distress monitor 100 is installed about another portion of the body of the patient 10, the distress monitor 100 may be attached to the patient 10 by a different wearable component. In an embodiment where the distress monitor 100 is installed in contact with the forehead of the patient 10, a headband with cut-outs to allow the electrodes of the EMG sensor 150, the electrodes of the GSR sensor 130, and/or the pulse sensor 140 to be in direct contact with the skin of the patient 10. The tracheostomy tie and the headband, as well as any other device that may be used to removably secure the distress monitor 100 to the patient so that the electrodes of the EMG sensor 150, the electrodes of the GSR sensor 130, and/or the pulse sensor 140 are in direct contact with the skin of the patient 10 can be referred to as a "wearable garment" herein.

The controller filters, amplifies, and performs an analog to digital (A2D) conversion of the signals from each of the sensors 130, 140, and 150. The controller then transmits the data, either via a discrete communication device or a communication device that is integral to the controller, to the display (200, FIG. 6). In some embodiments, the controller is configured to perform further data analysis, such as pattern recognition and/or thresholding, before the data is transmitted to the display. In some other embodiments, the display comprises a controller which performs further data analysis, such as pattern recognition and/or thresholding.

Figure 6:
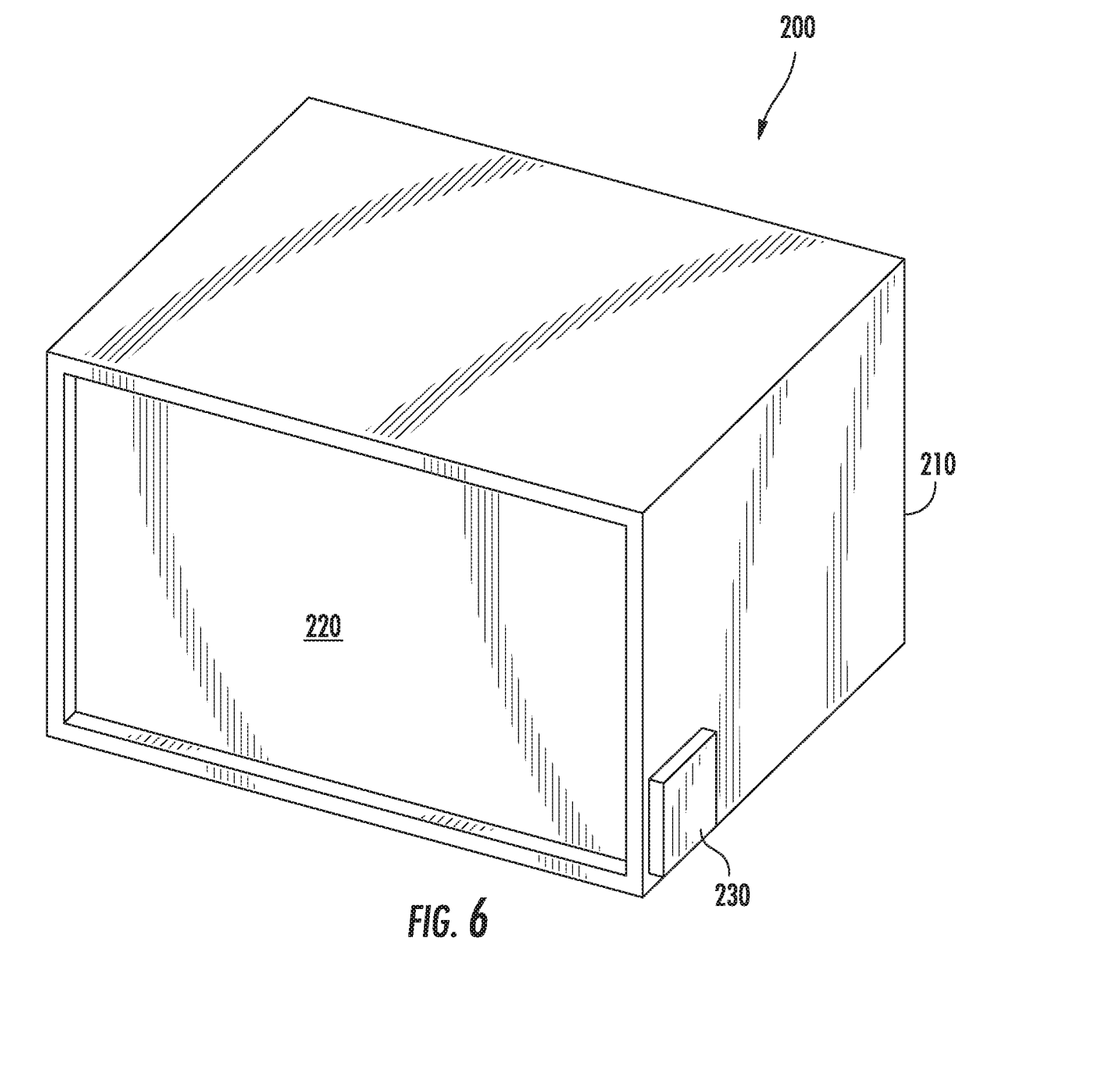
FIG. 6 is an isometric view of an example embodiment of a wireless monitoring device for use in receiving and displaying outputs from the band shown in FIG. 1A, in accordance with the disclosure herein.

The display 200 is shown in FIG. 6. In the embodiment shown, the display 200 comprises a housing 210, with a screen 220 and a data processor 230 In one embodiment, the display 200 will receive, at the data processor 230, the output data from the controller of the distress monitor 100. The data processor 230 may have a wireless radio to receive a wireless transmission from the controller 180 of the distress monitor 100. The wireless radio may be configured to receive and/or transmit data over any suitable communication medium and/or protocol, including, for example, via Wi-Fi, Bluetooth, NFC, RFID, ethernet, fiber optics, and the like. The display 200 may be connected to alternating or direct current sources, including power from a wall plug (e.g., at 110V and/or 22V0V) and/or from a rechargeable battery. The data processor 230 will analyze the data received, for example, by applying pattern recognition and/or thresholding algorithms to integrate data from each of the sensors 130, 140, and 150 to determine when the patient 10 is in distress. It is advantageous, using the thresholding algorithm, for at least two of the three sensors being monitored to reach a threshold before triggering an alarm. The output of each sensor will use different thresholding values. The algorithms will integrate information from the EMG, pulse, and GSR sensors 130, 140, 150 to determine states of distress in the patient 10. The screen 220 may provide visualizations of the data and any results of the analysis from the data processor 230 in a manner that is readily understood by caregivers (e.g., numerical, pictorial, graphical, and the like). In some embodiments, the visualizations on the screen 220 include pulse rate, blood oxygen level, and/or any distress indications. In some embodiments, the display 200 may be a personal electronic devices, such as, for example, a mobile phone, a tablet, a wearable device, such as a watch or activity tracker, a piece of jewelry, or the like.

In some embodiments, the controller and/or the data processor 230 may be programmed to analyze the data from the sensors 130, 140, 150 to detect changes in frequency of any of the signals. A thresholding algorithm is used to distinguish between baseline signal levels and changes. The controller and/or the data processor 230 tracks changes in the signals for each of the sensors 130, 140, 150. When the signals reach a threshold, the controller and/or the data processor 230 may generate an audible alert to inform and/or notify caregiver(s) that the patient 10 is in a state of distress. In some embodiments, the display 200 can be a computing device or a personal electronic device, including, for example, a smart phone or tablet.

The electromyography (EMG) sensors 130 comprise electrodes that act as positive and negative leads, respectively. Electrical ground is on the controller within the electronics region 120 of the distress monitor 100. The EMG sensors 130 are electrically connected to the controller and adhesively (e.g, integrally) connected to the band 110. Through contact with the skin of the patient, the EMG sensors 130 measures the electromyography signals of the neck muscles of the patient 10 to detect distress of the patient 10. The heart rate, or pulse, sensor 140 can be any suitable type of pulse sensor. However, in the embodiment shown, the pulse sensor 140 is an optical sensor that is electrically connected to the controller and adhesively (e.g., integrally) connected to the band 110. The galvanic skin response (GSR) sensors 150 comprises electrodes that act as positive and negative leads, respectively. Electrical ground is on the controller within the electronics region 120 of the distress monitor 100. The GSR sensors 150 are electrically connected to the controller and adhesively (e.g, integrally) connected to the band 110. Through contact with the skin of the patient, the GSR sensors 150 measure galvanic skin response signals that occur due to changes in skin conductance that occur during times of physiological distress due to sympathetic nervous system states. In some embodiments, the distress monitor 100 is insertable and removable from the tie, headband, or other wearable device by which the distress monitor 100 is secured to the patient 10 so that the electrodes of the EMG sensor 150, the electrodes of the GSR sensor 130, and/or the pulse sensor 140 are in direct contact with the skin of the patient 10.

Figure 7:
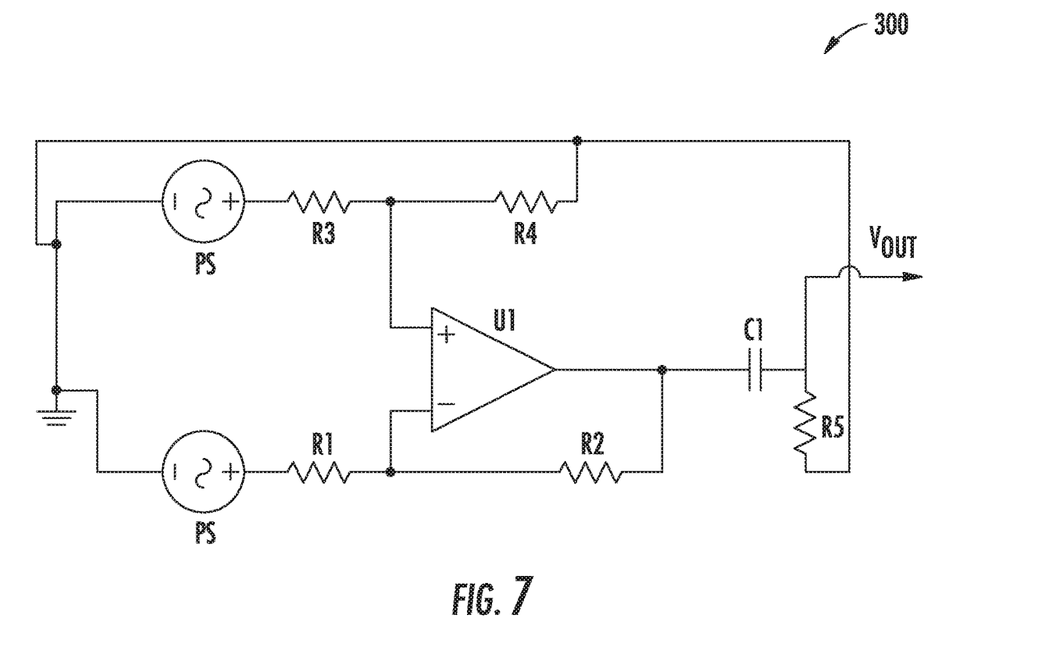
FIGS. 7-9 are electrical schematic diagrams for respective signal conditioning circuits of the band shown in FIG. 1A, in accordance with the disclosure herein.

FIG. 7 is a diagram, generally designated 300, for an example embodiment of a circuit for amplifying and filtering the signals from the EMG sensors 130. The EMG circuit 300 conditions the EMG signal from the EMG sensors 130 before the signal is transmitted to the controller of the distress monitor 100. The circuit comprises a differential amplifier U1 having a gain of 30,000 and a high pass filter. The high pass filter acts to filter out signals that are artifacts of movement by the patient, such as a movement of the neck, that would otherwise distort the EMG signal. In the embodiment shown here, the filter used is a passive filter. After having been filtered and amplified, the signal is transmitted to the controller at Vout. The positive and negative power terminals provide 1 Volt at 1 kHz, with a 0° phase angle. Resistors R1 and R3 are 1kΩresistors. Resistors R2 and R4 are 300kΩresistors. Resistor R5 is a 2kΩresistor. Capacitor C1 is a 4 μF capacitor.

Figure 8:
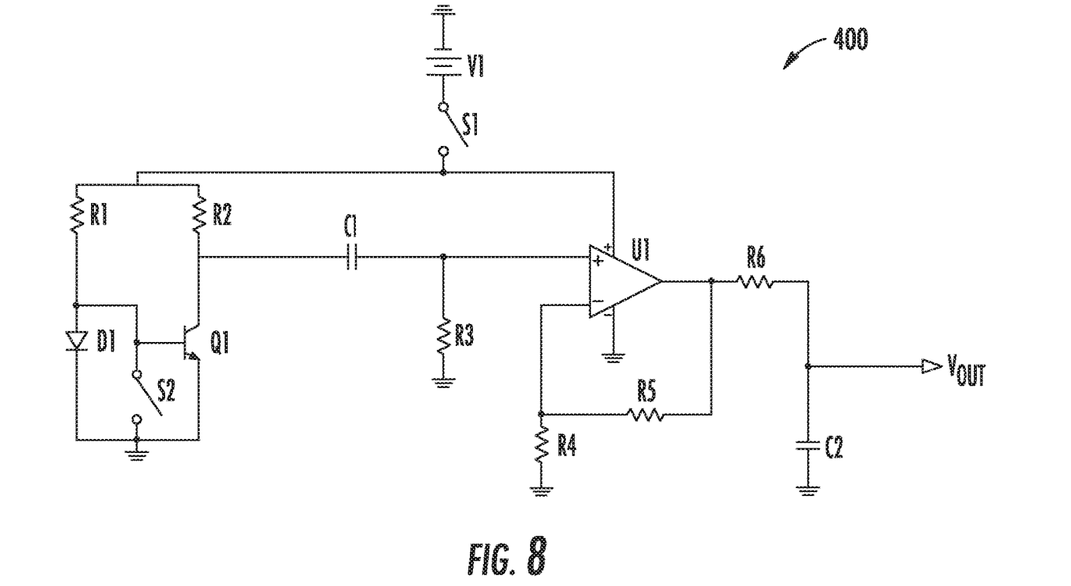

FIG. 8 is a diagram, generally designated 400, for an example embodiment of a circuit for amplifying and filtering the signals from the pulse sensor 140. The pulse circuit 400 is used to condition a signal from a pulse sensor, which can also be a combination pulse-oxygen sensor, that is able to detect a blood oxygen content and pulse of the patient. Diode D1, transistor Q1, and switch S2 forms a phototransistor that can detect light, which is generated by the diode and incident on the patient's skin, being reflected back through the blood of the patient. The impulse that is generated when the light is received is transmitted through a differential amplifier U1, which can be an MCP6273 Op-Amp, to amplify the signal by a gain of approximately 110 to make the signal easier to read. The amplified signal is then transmitted to the controller of the distress monitor 100. The number of impulses in a given time period (e.g., a minute) will correspond to the pulse of the patient. Resistors R1, R4, and R6 are 220Ωresistors. Resistors R2 and R3 are 10kΩresistors. Resistor R5 is a 2.7MΩresistor. Capacitors C1 and C2 are 10 μF capacitors. Voltage source V1 is a direct current source at a potential of 3 volts. S1 and S2 are switches. Q1 is a 100A/A transistor.

Figure 9:
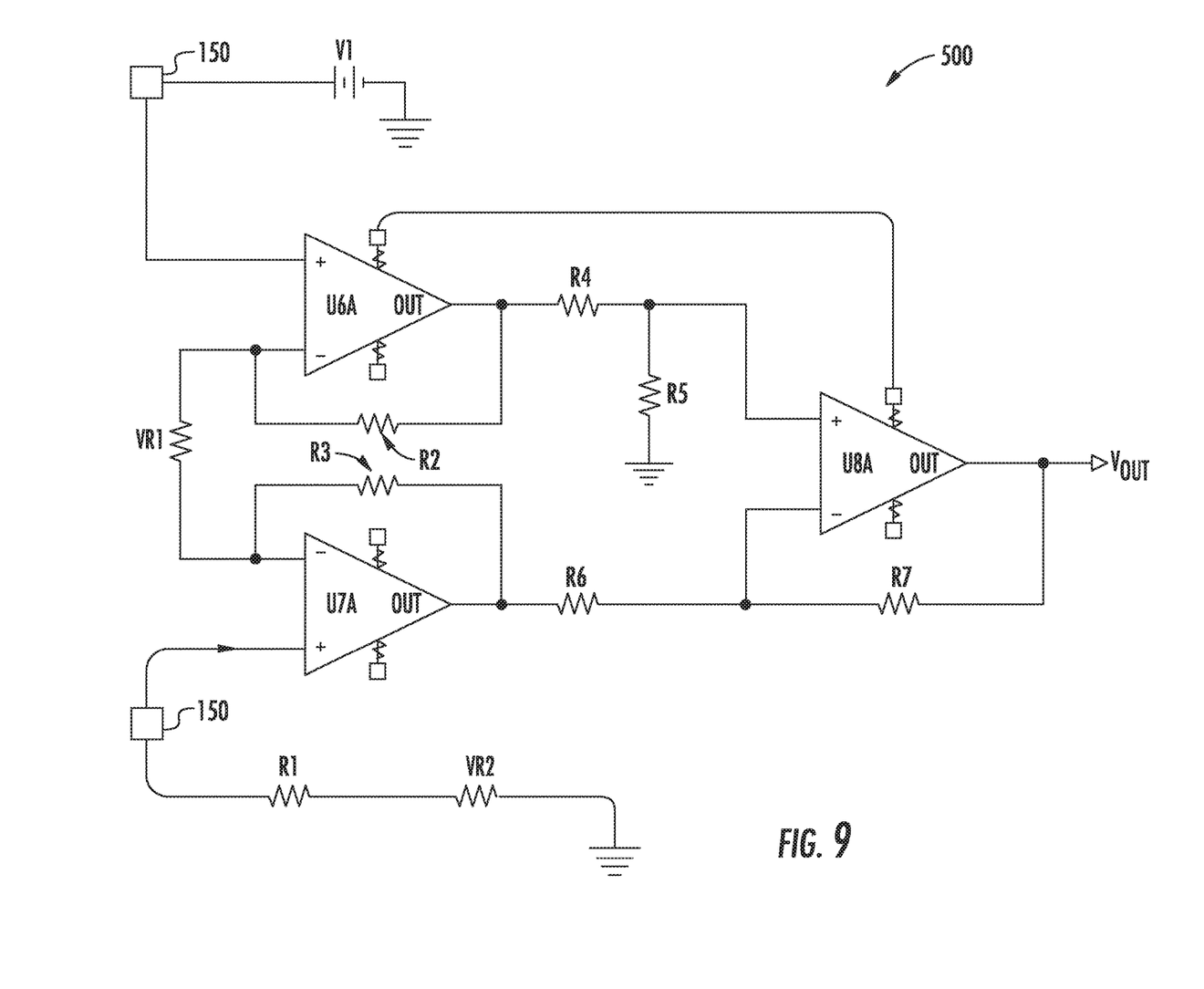

FIG. 9 is a diagram, generally designated 500, for an example embodiment of a circuit for amplifying and filtering the signals from the GSR sensors 150. The GSR circuit 500 is used to condition the signal generated by the GSR sensors 150. A GSR sensor 150 comprises two electrodes that measure the conductivity of the skin of the patient 10, which conductivity changes when the sweat glands are more active, which can be an indicated that the body of the patient is going into a sympathetic nervous state. The sympathetic nervous response is an indicator of physiological distress. The GSR circuit 500 has differential amplifiers U6A, U7A, and U8A, which measure the difference in the signals from the two electrodes of the GSR sensor 150, and a high pass filter. The amplifiers U6A, U7A, and U8A enable the signal(s) from the electrodes to be read more easily. Resistor R1 is a 1MΩresistor. Resistors R2 and R3 are 100kΩresistors. Resistors R4, R5, R6, and R7 are 10kΩresistors. Varistor VR1 is a 100kΩvariable resistor. Varistor VR2 is a 1MΩvariable resistor. Voltage source V1 is a direct current source, such as a battery, that provides 1.5 volts.

Figure 10:
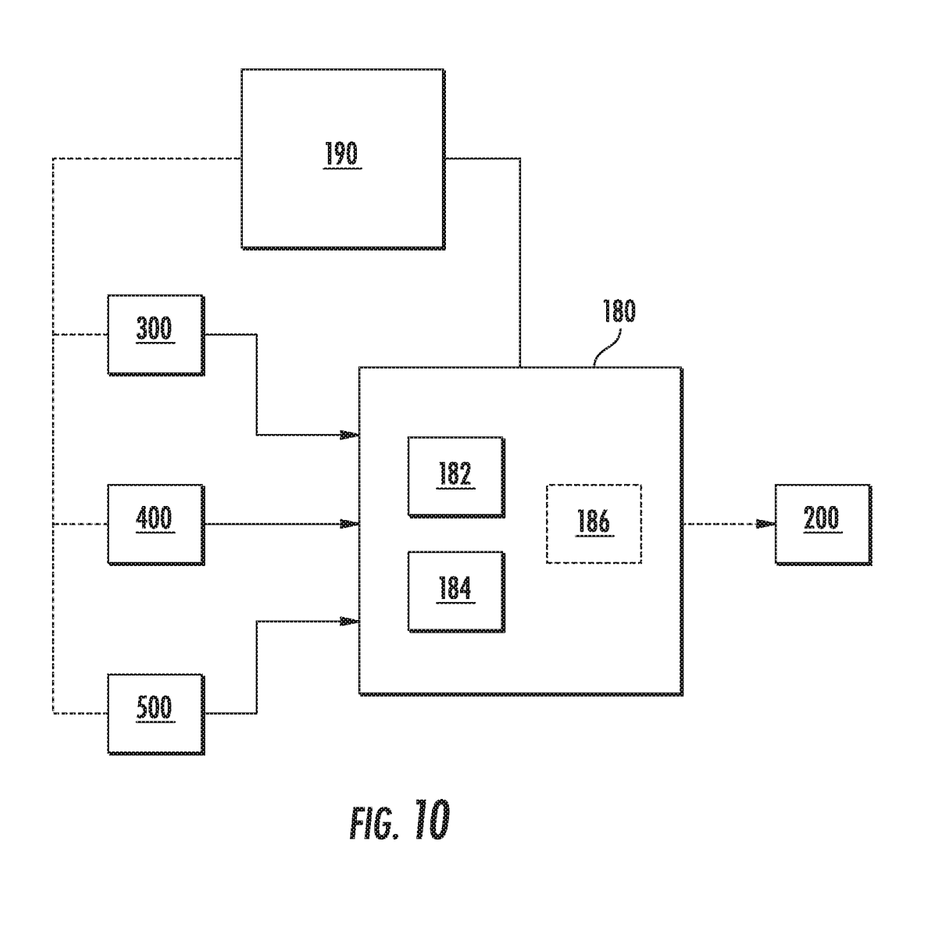
FIG. 10 is a schematic illustration showing the interconnection between the electrical circuits of FIGS. 7-9, the controller of the band of FIG. 1A, and the wireless monitoring device of FIG. 6, in accordance with the disclosure herein.

FIG. 10 is a schematic block diagram showing that the output signals from the EMG circuit 300, the pulse circuit 400, and the GSR circuit 500 are input to the controller 180, which is housed within the electronics region 120 of the distress monitor shown in FIGS. 1A-5. The controller 180 comprises a processor 182, a memory 184, and, optionally, a wireless communication chip 186. The processor 182 executes various signal analysis algorithms that are stored, for example, in the memory 184 or in a storage device, including, for example pattern recognition and/or thresholding, to the outputs from the EMG, pulse, and GSR circuits 300, 400, 500. In some embodiments, the processor 182, the memory 184, the wireless communication chip 186, and/or the storage can be integrated and/or fabricated into a single system-on-chip (SoC) design. The controller 180 transmits a status signal, which can be activated only upon issuance of an alert or a constant status regardless of alert status, to the display 200. In the embodiment shown, the data transmission to the display 200 is via a wireless communication protocol (e.g., Wi-Fi, Bluetooth, NFC, RFID, and the like), but it is envisioned that a wired connection may be possible as well. However, the wireless transmission is advantageous because it does not require wires in which the patient could become entangled during use. A power source 190 can be connected to provide power to the controller 180 and/or any of the EMG, pulse, and GSR circuits 300, 400, 500. The power source 190 can be any of a disposable battery, a rechargeable battery of any suitable battery chemistry, a supercapacitor, an alternating current source, and/or a direct current power source.

The subject matter disclosed herein can be implemented in software in combination with hardware and/or firmware. For example, the subject matter described herein can be implemented in software executed by a processor or processing unit. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

While at least one example embodiment of the invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise.

Other embodiments of the current invention will be apparent to those skilled in the art from a consideration of this specification or practice of the invention disclosed herein. Thus, the foregoing specification is considered merely exemplary of the current invention with the true scope thereof being defined by the following claims.

What is claimed is:

1. A system for monitoring physiological indicators that a patient is in distress, the system comprising:
   a distress monitor comprising:
      a band configured to be placed about and in contact with a portion of a body of the patient, wherein the patient is a pediatric patient with a tracheostomy tube installed in a trachea of the patient, so that the patient cannot verbally communicate distress;
a plurality of sensors configured to measure changes in the physiological indicators of the patient; and
a controller contained within an electronics region of the band, the controller being electronically connected to each of the plurality of sensors to receive a respective output signal from each; and
a display configured to receive an output signal from the controller and to display an alert when the patient is displaying indicators of physiological distress.

2. The system of claim 1, wherein the band comprises a passage formed through a thickness thereof, through which the tracheostomy tube can pass.

3. The system of claim 1, wherein the plurality of sensors comprise a pulse sensor, an electromyography (EMG) sensor, a galvanic skin response (GSR) sensor, or any combinations of the pulse sensor, the EMG sensor, and the GSR sensor, wherein the EMG sensor comprises at least two electrodes arranged on opposite sides of the neck of the patient, the EMG sensor being configured to detect movement of muscles in the neck of the patient, wherein the pulse sensor is an optical heart rate sensor, wherein the GSR sensor comprises at least two electrodes in direct contact with a surface of a skin of the patient to detect changes in conductance in the skin in response to distress.

4. The system of claim 3, comprising a wearable garment configured to secure a tracheostomy tube and the distress monitor to a neck of the patient, wherein the wearable garment is a tracheostomy tie configured to secure a tracheostomy tube and the distress monitor to a neck of the patient.

5. The system of claim 4, wherein the wearable garment has a plurality of holes formed in a surface of which is arranged directly against the skin of the patient, so that electrodes of the EMG sensor, electrodes of the GSR sensor, and/or the pulse sensor are in direct contact with the skin of the patient.

6. The system of claim 1, wherein the controller is configured to execute one or more algorithms to analyze an output signal of each of the plurality of sensors.

7. The system of claim 1, wherein the display comprises a data processor configured to execute one or more algorithms to analyze an output signal of each of the plurality of sensors.

8. The system of claim 1, wherein the display is configured to display information regarding the physiological indicators of the patient and/or an alert when at least two physiological indicators indicate that the patient is in distress.

9. The system of claim 8, wherein the alert is an audible alert, a visual alert, a haptic alert, or any combination thereof.

10. The system of claim 1, wherein the controller is configured to generate an alert when the plurality of sensors are active but one or more of the plurality of sensors are not transmitting an output signal to the controller due to an improper installation of the distress monitor on the patient and/or one or more of the plurality of sensors is malfunctioning.

11. A method of monitoring physiological indicators to detect when a patient is in distress, the method comprising:
attaching a distress monitor to the patient, wherein the patient is a pediatric patient with a tracheostomy tube installed in a trachea of the patient, so that the patient cannot verbally communicate distress, the distress monitor comprising:
a plurality of sensors contained within and/or on a surface of a band of the distress monitor; and
a controller contained within an electronics region of the band, the controller being electronically connected to each of the plurality of sensors;
measuring, using the plurality of sensors, changes in the physiological indicators of the patient;
transmitting an output signal for each of the plurality of sensors to the controller;
applying one or more algorithms to analyze the output signal for each of the plurality of sensors; and
generating an alert when at least a plurality of the physiological indicators indicate that the patient is in distress.

12. The method of claim 11, wherein the alert is transmitted to a display, the alert comprising one or more of an audible alert, a visual alert, a haptic alert, or any combination thereof.

13. The method of claim 11, wherein the plurality of sensors comprise a pulse sensor, an electromyography (EMG) sensor, a galvanic skin response (GSR) sensor, or any combinations of the pulse sensor, the EMG sensor, and the GSR sensor, wherein the EMG sensor comprises at least two electrodes arranged on opposite sides of the neck of the patient, the EMG sensor being configured to detect movement of muscles in the neck of the patient, wherein the pulse sensor is an optical heart rate sensor, wherein the GSR sensor comprises at least two electrodes in direct contact with a surface of a skin of the patient to detect changes in conductance in the skin in response to distress.

14. The method of claim 13, comprising securing the distress monitor to a neck of the patient via a wearable garment, wherein the wearable garment is a tracheostomy tie that secures a tracheostomy tube and the distress monitor to a neck of the patient.

15. The method of claim 14, wherein the wearable garment has a plurality of holes formed in a surface thereof which is arranged directly against the skin of the patient, the method comprising:
inserting the distress monitor within the wearable garment; and
securing the wearable garment to the patient so that electrodes of the EMG sensor, electrodes of the GSR sensor, and/or the pulse sensor are in direct contact with the skin of the patient.

16. The method of claim 11, wherein the display comprises a data processor, the method comprising:
transmitting an output of each of the plurality of sensors to the display; and
executing, via the data processor, one or more algorithms to analyze each output signal of each of the plurality of sensors.

17. The method of claim 16, comprising displaying information on the display regarding the physiological indicators of the patient and/or an alert when at least two physiological indicators indicate that the patient is in distress.

18. The method of claim 11, comprising generating, using the controller, an alert when the plurality of sensors are active but one or more of the plurality of sensors are not transmitting an output signal to the controller due to an improper installation of the distress monitor on the patient and/or one or more of the plurality of sensors is malfunctioning.

* * * * *